US007556946B2

(12) United States Patent
Versali et al.

(10) Patent No.: US 7,556,946 B2
(45) Date of Patent: Jul. 7, 2009

(54) CELL WALL DERIVATIVES FROM BIOMASS AND PREPARATION THEREOF

(75) Inventors: Marie-France Versali, Tilff (BE); Fabienne Clerisse, Braives (BE); Jean-Michel Bruyere, Liège (BE); Sandrine Gautier, Liège (BE)

(73) Assignee: Kitozyme S.A., Herstal (BE)

( * ) Notice: Subject to any disclaimer, the term of this patent is extended or adjusted under 35 U.S.C. 154(b) by 319 days.

(21) Appl. No.: 10/504,046

(22) PCT Filed: Feb. 12, 2003

(86) PCT No.: PCT/EP03/01375

§ 371 (c)(1),
(2), (4) Date: Jan. 28, 2005

(87) PCT Pub. No.: WO03/068824

PCT Pub. Date: Aug. 21, 2003

(65) Prior Publication Data
US 2005/0130273 A1 Jun. 16, 2005

(30) Foreign Application Priority Data
Feb. 12, 2002 (BE) ................. 2002/0093

(51) Int. Cl.
C12P 19/04 (2006.01)
C12P 1/02 (2006.01)
C08B 37/08 (2006.01)
C07H 1/06 (2006.01)
C07H 1/08 (2006.01)

(52) U.S. Cl. ................... 435/101; 435/171; 536/20; 536/127

(58) Field of Classification Search ............... 435/101, 435/171
See application file for complete search history.

(56) References Cited

U.S. PATENT DOCUMENTS

| 4,034,121 | A | 7/1977 | Denn et al. |
| 4,424,346 | A | 1/1984 | Hall et al. |
| 4,806,474 | A | 2/1989 | Hershberger |
| 4,810,646 | A | 3/1989 | Jamas et al. |
| 4,833,237 | A | 5/1989 | Kawamura et al. |
| 5,232,842 | A | 8/1993 | Park et al. |
| 5,739,015 | A | 4/1998 | Srinivasan |
| 6,255,085 | B1 * | 7/2001 | Chen et al. .............. 435/101 |
| 6,333,399 | B1 * | 12/2001 | Teslenko et al. ........... 536/20 |

FOREIGN PATENT DOCUMENTS

| DE | 196 36 702 | 3/1998 |
| DE | 199 60 632 | 7/2001 |
| EP | 0 230 378 | 7/1987 |
| EP | 0 542 249 | 11/1992 |
| EP | 0 913 407 | 5/1995 |
| EP | 1 067 197 | 1/2001 |
| EP | 1 247 819 | 10/2002 |
| EP | 1 306 390 | 5/2003 |
| FR | 2 701 266 | 8/1994 |
| WO | WO 91/15767 | 10/1991 |
| WO | WO 92/07064 | 4/1992 |
| WO | WO 93/07262 | 4/1993 |
| WO | WO 95/30022 | 11/1995 |
| WO | WO 01/68714 | 9/2001 |
| WO | WO 01/80915 | 11/2001 |
| WO | WO 03/011912 | 2/2003 |
| WO | WO 03/042251 | 5/2003 |
| WO | WO 03/051376 | 6/2003 |
| WO | WO 03/057768 | 7/2003 |
| WO | WO 03/086281 | 10/2003 |

OTHER PUBLICATIONS

Yokoi et al. Journal of Fermentation and Bioengineering. 1998, vol. 85, No. 2, pp. 246-249.*

Delben, et al. "Chelating Ability and Enzymatic Hydrolysis of Water-Soluble Chitosans," *Carbohydrate Polymers*, vol. 19, pp. 17-23, 1992.

Donglin, et al. Effects of Chitosan Coatinig on Enzymatic Browning and Decay During Postharvest Storage of Litchi (*Litchi chinensis* Sonn.) *Post Harvest Biology and Technology*, col. 12(2): 195-202, FSTA XP002172877, abstract only.

Fontaine, et al. "Molecular Organization of the Alkali-Insoluble Fraction of *Aspergillus fumigatus* Cell Wall," *Journal of Biological Chemistry*, vol. 275, No. 36, pp. 27594-27607, Sep. 8, 2000.

(Continued)

*Primary Examiner*—Vera Afremova
(74) *Attorney, Agent, or Firm*—Knobbe, Martens, Olson & Bear, LLP

(57) ABSTRACT

In a first aspect, the present invention relates to a method for isolating cell wall derivatives from fungal or yeast biomass. According to this method, chitin polymers or chitin-glucan copolymers can be obtained. In another aspect, the invention relates to a method for preparing chitosan from chitin. The invention further relates to chitin polymers, chitin-glucan polymers and chitosan polymers obtainable by the methods according to the invention. Moreover, the invention relates to the use of chitin polymers, chitin-glucan copolymers or chitosan polymers obtainable by the method according to the present invention in medical, pharmaceutical, agricultural, nutraceutical, food, textile, cosmetic, industrial and/or environmental applications.

4 Claims, 2 Drawing Sheets

OTHER PUBLICATIONS

Itoyama, et al. "Space Effects on Enzymatic Activity of Papain Immobilized Onto Porous Chitosan Beads," *Biomaterials*, vol. 15, No. 2, pp. 107-112, 1994.

Tatsumi, et al. "Removal of Phenols from Wastewater by an Enzyme and Chitosan," *Advances in Chitin Sciences*, vol. 2, pp. 864-869, 1997.

Database WPI, Section Ch, Week 199703, Derwent Publications, Ltd., London, GB; Class D13, AN 1997-028342, XP002241259 and JP 08 289785 A (Norinsuisansho Shokuhin Sogo), Nov. 5, 1996, abstract.

Database WPI, Section Ch, Week 198843, Derwent Publications Ltd., London, GB; Class A11, AN 1988-304874, XP002241260 and JP 63 225602 A (Nitta Gelatin KK), Sep. 20, 1988, abstract.

Kafetzopoulos, et al. "Bioconversion of Chitin to Chitosan: Purification and Characterization of Chitin Deacetylase from *Mucor rouxii*," *Proc. Natl. Acad. Sci. USA*, vol. 90, pp. 2564-2568, 1993.

Klis, "Review: Cell Wall Assembly in Yeast," *Yeast*, vol. 10, pp. 851-869, 1994.

Kollár, et al. "Architecture of the Yeast Cell Wall, The Linkage Between Chitin and a $\beta(1\rightarrow3)$-Glucan," *The Journal of Biological Chemistry*, vol. 270, No. 3, pp. 1170-1168, Jan. 20, 1995.

Manners, et al. "The Structure of a $\beta$-$(1\rightarrow3)$-D-Glucan from Yeast Cell Walls," *Journal of Biochemistry*, vol. 135, pp. 19-30, 1973.

Win, et al. "Shrimp Chitin as Substrate for Fungal Chitin Deacetylase," *Appl. Microbiol. Biotechnol.*, vol. 57, Issue 3, pp. 334-341, 2001, Abstract.

Hu, et al. "Rapid Extraction of High-quality Chitosan from Mycelia of *Absidia glauca,:*" *Journal of Food Biochemistry*, vol. 23, pp. 187-196, 1999.

Kollart, et al. "Architecture of the Yeast Cell Wall," *The Journal of Biological Chemistry*, vol. 370, No. 3, pp. 1170-1178, Jan. 30, 1996.

Yamaoka, et al. "The Structure of Chitin-Glucan Complex Isolated from Yeast Bud Scars," *Agric. Biol. Chem.*, vol. 53, No. 5, pp. 1255-1259, 1989.

\* cited by examiner

CELL WALL DERIVATIVES FROM BIOMASS AND PREPARATION THEREOF

RELATED APPLICATIONS

This application is the U.S. National Phase under 35 U.S.C. § 371 of International Application PCT/EP03/01375, filed Feb. 12, 2003, which claims priority of BE 2002/0093, filed Feb. 12, 2002.

FIELD OF THE INVENTION

In a first aspect, the present invention relates to a method for isolating cell wall derivatives from fungal or yeast biomass. In another aspect, the invention relates to a method for preparing chitosan from chitin. The invention further relates to chitin polymers, chitin-glucan copolymers and chitosan polymers obtainable by the methods according to the invention. Moreover, the invention relates to the use of chitin polymers, chitin-glucan copolymers or chitosan polymers obtainable by the methods according to the present invention in pharmaceutical, medical, agricultural, nutraceutical, food, textile, cosmetic, industrial and/or environmental applications.

BACKGROUND OF THE INVENTION

Natural polysaccharides such as starch, cellulose or chitin are of great technological importance, as there are easily available in massive amounts, and as they present unique characteristics often not found for synthetic polymers. For example, cells walls of fungi are organized by a network of polysaccharides, proteins, lipids, the major part of the polysaccharide chains being β-glucans and chitin.

Chitin is a natural high molecular weight polymer widely found in nature, in fact the second major biopolymer after cellulose. Chitin is a polysaccharide whose structure is close to that of cellulose. It is the main component of insect and crustacean cuticule, and is also part of the cell walls of some fungi and other organisms. Chitosan is produced at the industrial level by chemical modification of chitin, and is naturally found in a few organisms. Chitin is the linear polymer of N-acetyl-(D)-glucosamine linked through a β(1.4) osidic bond, that can be represented by Formula I. Chitosan is the random copolymer of N-acetyl-(D)-glucosamine and (D)-glucosamine, that can be represented by Formula II. Chitin and chitosan are part of the glycosaminoglycan family of polymers.

Similar to cellulose, chitin is a fibrous polysaccharide that has additional chemical and biological properties useful in many industrial and medical applications. Nevertheless, chitin is more difficult to extract, since it is usually found in its natural structure in which it is closely associated with other substances.

Chitosan can be prepared by partial hydrolysis of the acetyl groups of the N-acetyl-glucosamine units, so that the polymer becomes soluble in dilute solution of most acids. Chitosan can be derived from a polymer extracted from biomass, chitin. It is defined by two molecular characteristics, the average molecular weight and the degree of acetylation, that is the proportion of acetylated glucosamine units along the polymer backbone.

Formula I:

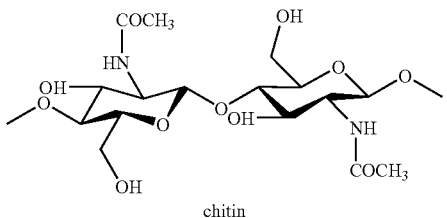

chitin

Formula II:

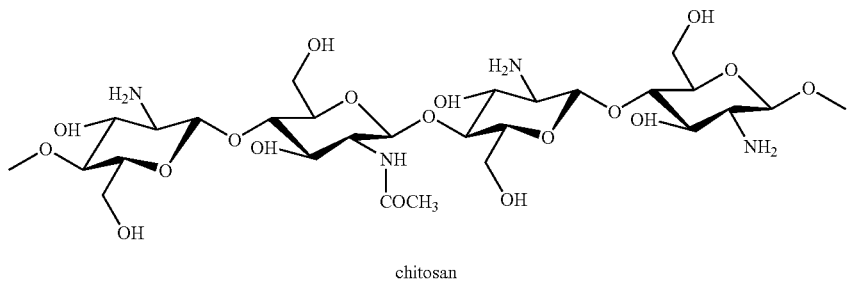

chitosan

Industrial production of chitin and chitosan is generally exploiting wastes of crustacean shells, for instance crab or shrimp shells. Two steps, decalcification by acidic treatment and deproteneisation by alkaline treatment, allow chitin isolation, followed by a deacetylation step by using a hot concentrated alkaline solution. However chitin produced from crustacean biomass often contains high levels of minerals, mainly calcium carbonate, whose amount can reach up to 90% of chitin dry weight. The quality of chitin and chitosan is therefore often non reproducible and dependent on seasonal variation and crustacean species. The deacetylation method is a degrading one, and chitosan is often of very variable molecular weight and degree of acetylation, which makes product development by users more difficult. Moreover, high production costs result from the requirement of a huge calorific energy, and of large amounts of sodium hydroxyde, as well as the extensive acidic treatment required by the separation of chitin from calcium carbonate, whose amount can reach up to 90% of chitin dry weight.

Alternative sources for chitin and chitosan however do exist, like for instance fungi whose cell walls can contain up to 40% of the wall dry weight. The fungal mycelium is a complex network of filaments made of cells. The mycelium cell walls are made of hemicellulose, chitin and β-glucans. Fungi which contain sufficient amounts of chitin can be selected and grown specifically for the extraction of chitin. Furthermore, by-products of industrial fermentation process, such as the biomass collected after fungi or yeasts fermentation, also contain chitin associated with other biopolymers, mainly glucans, mannans, proteins and lipids. These fermentation by-products are generally burnt right after separation from the culture medium, because their storage is not economically relevant.

For chitin and chitosan to be used in as many applications as possible, their quality should be uniform and pure. The production of chitosan from a pure chitin, which would be available in large amounts in a reproducible way and would contain low amounts of inorganic and protein impurities would therefore be a substantial progress in this field.

The state of the art regarding alternative sources of chitin and chitosan to the crustacean ones is not very wide. A few patent and patent applications refer to fungal mycelium as a potential industrial source of chitin, for instance patents U.S. Pat. Nos. 4,960,413, 6,255,085, 4,195,175, 4,368,322, 4,806,474, 5,232,842, 6,333,399, and patent applications WO 01/68714, GB-A-458,839, GB-A-2,026,516, GB-A-2,259,709, DE-A-2,923,802 et RU-C-2,043,995. Most of these documents disclose methods for preparing chitosan or chitosan-glucan from fungal mycelium. Moreover, the methods describe direct transformation of chitin contained in the fungal cell walls, without any intermediate step for the isolation and purification of chitin. Therefore the methods described in these patents and patent applications do not allow the isolation of pure chitin as a source of pure chitosan. In these methods, highly concentrated alkaline solutions and severe temperature and duration conditions are employed, which again bring high pollution risks. Furthermore, these aggressive processes probably yield very low molecular weight chitin derivatives and chitosan, and cannot be used for the production of higher molecular weight chitosan.

Other articles describe fundamental studies of the cell wall structure of some fungal species, for example, Hartland et al. (1994) *Yeast* 10, 1591-1599; Hong et al. (1994) *Yeast,* 10, 1083-1092; Hearn et al. (1994) *Microbiology* 140, 789-795; Fontaine et al. (2000) *Journal of Biological Chemistry* 275, 27594-27607. These studies consistently conclude that the cell walls are made mainly of chitin and beta-glucans, and that the two types of polymer chains are closely associated, probably through covalent bonds in most fungi. Some of these studies mention the use of specific enzymes to selectively degrade the components of the cell walls, namely glucanases and chitinases, in order to further identify residual sugars to be able to estimate the initial polysaccharide composition. It is in general an object of the present invention to provide an improved method for the isolation of cell wall derivatives from fungal or yeast biomass. It is in particular an object of the present invention to provide a method for isolating chitin polymers or chitin-glucan polymers. It is another object of the present invention to provide a method for preparing chitosan.

Another object of the invention is to isolate chitin polymers and to prepare chitosan following a rapid process that does not require high-energy consumption nor chemicals that would be detrimental to the environment.

Another aspect of the invention is to provide a method to isolate pure chitin polymers and to prepare chitosan polymers from non-animal origin, which are suitable for applications in various fields.

The present invention also aims to provide polymers of chitin having a high degree of purity. Moreover, it is another object of the present invention to provide chitin-glucan copolymers wherein the amount of chitin and beta-glucan is adjustable. The present invention further aims to provide chitosan having a high degree of purity and a controllable degree of acetylation and molecular weight.

SUMMARY

In a first aspect, the present invention relates to a method for isolating cell wall derivatives from fungal or yeast biomass comprising the subsequent steps of:
  a) contacting said biomass with a basic solution, whereby an alkali-soluble fraction and an alkali-insoluble fraction are obtained and whereby said alkali-soluble fraction is discarded and said alkali-insoluble fraction comprising said cell wall derivatives is retained,
  b) contacting said alkali-insoluble fraction with an acidic solution, by suspending said alkali-insoluble fraction and bringing said suspended fraction into contact with said acidic solution in order to obtain a suspension of acidified alkali-insoluble fraction comprising said cell wall derivatives, and
  c) contacting said acidified suspension of alkali-insoluble fraction with β-glucanase enzymes whereby said cell wall derivatives are obtained.

The fungal or yeast biomass treated in the present method according to the invention is made of fungi or yeast cells, of which the cell walls contain chitin. Alternatively, said biomass may also be a side-product of an industrial cultivation process wherein a fungal or yeast culture is used.

The invention provides a method that avoids the main drawbacks of existing methods. More particularly, the invention provides a chitin isolation method with economical and environmental advantages over existing methods and sources. More particularly, the invention discloses a method that allows separating chitin from β-glucans in a controlled way, without degradation or transformation of the chitin chains.

In a preferred embodiment, the invention relates to a method wherein said cell wall derivatives obtained in step c) are chitin polymers or chitin-rich chitin-glucan copolymers. More in particular, the invention relates to a method for the isolation of chitin from fungal or yeast biomass in order to obtain chitin polymers, essentially free of other polysaccharides like β-glucans.

The term "chitin polymers" refers to chitin polymers that contain more than 80% of chitin and less then 20% of beta-glucan, and preferably more than 90% of chitin and even more preferred more than 95% chitin.

The term "chitin-rich chitin-glucan copolymers" refers to polymers, which comprise chitin polymers as well as glucan polymers in certain relative amounts, but having a higher relative amount of chitin than of glucan. The method according to the invention enables to specifically adjust the amounts of chitin and glucan in these chitin-glucan copolymers. The amount of chitin in the copolymers can be adjusted by controlling the conditions of the enzymatic hydrolysis step in the present method. The invention thus provides a method for obtaining copolymers comprising chitin with a controllable purity. The term "polymers comprising chitin with controllable purity" refers to a polymer product wherein the amount of chitin can be adjusted in a controllable way by means of glucanase enzymes. In a preferred embodiment, the amount of chitin in said chitin-rich chitin-glucan copolymers is adjustable and preferably higher than 75% and even more preferably higher than 80%.

In another preferred embodiment, the invention relates to a method wherein said cell wall derivatives obtained in step a) or b) are chitin-glucan copolymers, from which the relative amounts of chitin over glucan depend on the used biomass.

The term "chitin-glucan copolymers" as used herein refers to copolymers obtained after extraction of fungal or yeast biomass but before enzymatic reaction by means of glucanase enzymes. The amount of chitin in said chitin-glucan copolymers is defined by the organism from which it is extracted. In a preferred embodiment, mycelium of *Aspergillus niger* is used in the method according to the invention, and chitin-glucan copolymers extracted from the mycelium of *Aspergillus niger* comprise between 30 and 50% (w/w) of chitin and between 50 to 70% of beta-glucan.

The terms "chitin" and "chitin polymers" are used herein as synonyms. In addition, the terms "chitosan" and "chitosan polymers" are used herein as synonyms.

In a second aspect, the present invention relates to a method for preparing chitosan from chitin comprising the subsequent steps of:
a) contacting said chitin with a basic solution, whereby an alkali-soluble fraction and an alkali-insoluble fraction is obtained and whereby said alkali-soluble fraction is discarded and said alkali-insoluble fraction comprising partially deacetylated chitin is retained,
b) contacting said alkali-insoluble fraction with an acidic solution, by suspending said alkali-insoluble fraction and bringing said suspended fraction into contact with said acidic solution in order to obtain an acidified alkali-insoluble fraction comprising said partially deacetylated chitin, and
c) contacting said acidified fraction with a chitin deacetylase, whereby chitosan is obtained.

In this aspect, the invention provides a method for preparing chitosan, whereby high molecular weight chitosan, with controlled degree of acetylation, by an enzymatic deacetylation reaction of chitin with a chitin deacetylase enzyme. In this aspect, the invention also provides a method for preparing chitosan whereby a low and medium molecular weight chitosan with a controllable degree of acetylation can be obtained.

The term "low and medium molecular weight" refers to an average molecular weight lower than 100 kDa, as measured by Ubbelohde capillary viscosimetry. The term "high molecular weight" refers to an average molecular weight higher than 100 kDA, as measured by capillary Ubbleohde viscosimetry.

The term "chitosan having a controlled degree of acetylation" refers to a product wherein the degree of acetylation, that is the proportion of N-acetyl-glucosamine units, can be adjusted in a controllable way.

In a preferred embodiment, the invention relates to a method wherein said chitin is fungal or yeast chitin obtainable by the method for isolating cell wall derivatives from fungal or yeast biomass according to the present invention. Since this source of chitin comprises a very high degree of purity, the invention allows preparing chitosan, which also yields a high degree of purity. In addition, this method also provides chitosan having an adjustable degree of acetylation, since the degree of acetylation can be adjusted by controlling the conditions of the enzymatic deacetylation in the present method.

In another aspect, the invention relates to a method for preparing chitosan from fungal or yeast chitin comprising the subsequent steps of:
a) contacting said chitin with a basic solution, whereby an alkali-soluble fraction and an alkali-insoluble fraction is obtained and whereby said alkali-soluble fraction is discarded and said alkali-insoluble fraction is retained,
b) contacting said alkali-insoluble fraction with an acidic solution, by suspending said alkali-insoluble fraction and bringing said suspended fraction into contact with said acidic solution whereby an acid-insoluble fraction and an acid-soluble fraction is obtained and whereby said acid-insoluble fraction is discarded and said acid-soluble fraction comprising chitosan is retained.

In this aspect, the invention provides a method for preparing chitosan, which yields low and medium molecular weight. This method comprises an alkaline hydrolysis reaction of chitin obtained from fungal or yeast biomass. The term "low and medium molecular weight" refers to an average molecular weight lower than 100 kDa, as defined above.

In another aspect, the present invention relates to chitin polymers obtainable by the method according to the present invention.

In addition, the invention also relates to chitin-rich chitin-glucan copolymers obtainable by the method according to the present invention.

The invention further relates to chitosan polymers obtainable by the method according to the present invention.

The invention further relates in another aspect to a composite material comprising chitin polymers, chitin-rich chitin-glucan copolymers or chitosan polymers obtainable by the method according to the present invention.

In another aspect, the invention relates to the use of chitin polymers, chitin-rich chitin-glucan copolymers or chitosan polymers obtainable by the method according to the present invention in medical, pharmaceutical agricultural, nutraceutical, food, textile, cosmetic, industrial and/or environmental applications.

Those skilled in the art will immediate recognize the many other effects and advantages of the present methods and the numerous possibilities for end uses of the present invention from the detailed description and examples provided below.

DETAILED DESCRIPTION OF THE FIGURES

DETAILED DESCRIPTION OF THE INVENTION

Method for Isolating Cell Wall Derivatives

Figure 1:
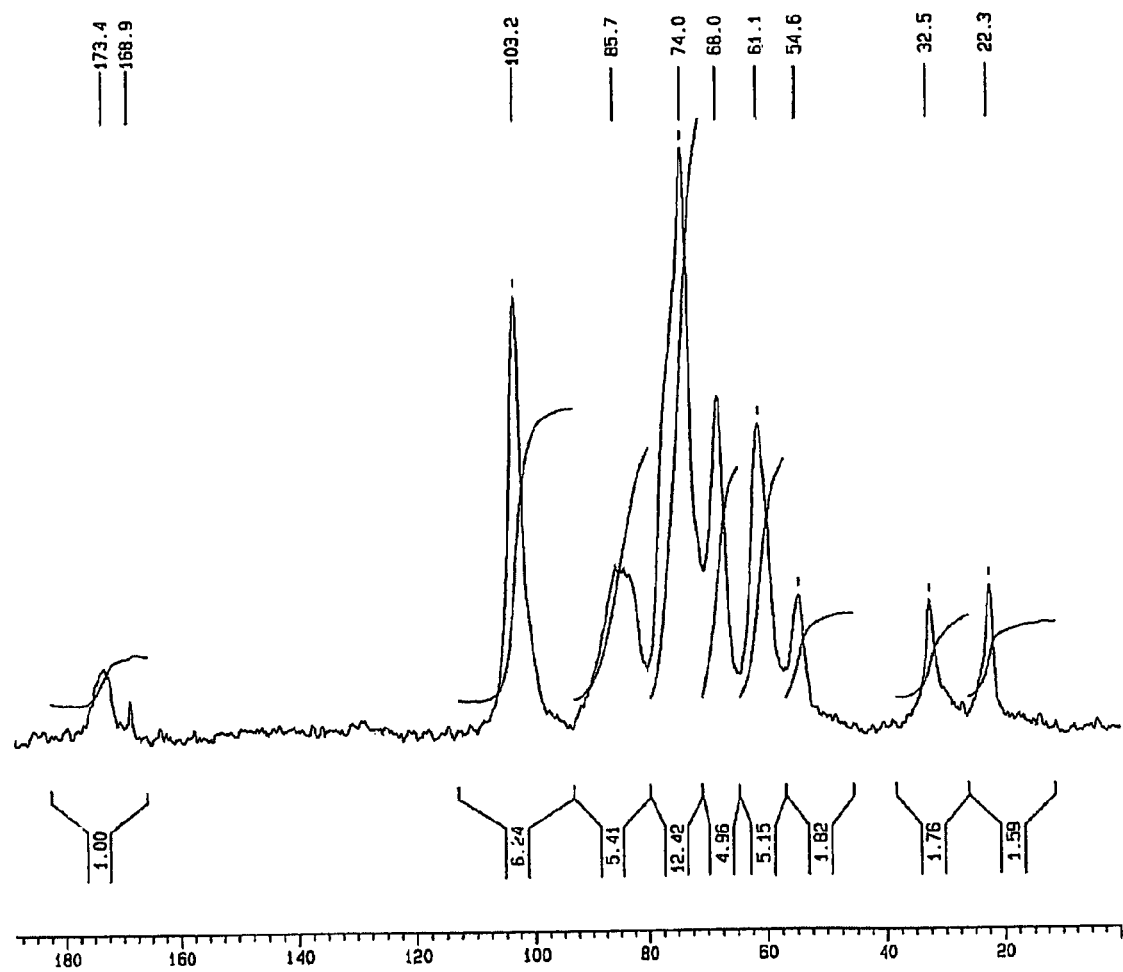
FIG. 1 represents the solid-state $^{13}$C-NMR spectrum of the alkali-insoluble fraction comprising a purified chitin-glucan polymer obtained after alkaline digestion of fungal biomass according to the first step in the method for isolating cell wall derivates of the present invention. The calculated chitin-glucan ratio is 41:59 (w/w).

The invention discloses in a first aspect a method for isolating cell wall derivatives from fungal and yeast biomass comprising the steps as described above.

In a preferred embodiment, the invention relates to a method characterized in that said cell wall derivatives are chitin polymers. The term "polymers" as used herein refers to high molecular weight substances that are mixtures of chains made by the repetition of one or several types of monomeric units. Generally, polymers are made of at least three monomeric units. The monomeric unit is the repeating unit that constitutes the polymeric chains. The term "chitin polymers" refers to a polymer made of at least 3 monomeric repeating units of β(1,4)-N-acetyl-(D)-glucosamine, and preferably more than 10, and even more preferably more that 20 monomeric units. Chitin polymers are chains of monomeric β(1,4-N-acetyl-(D)-glucosamine units linked through a covalent β(1-4) osidic bond.

The present invention provides a method, which enables extracting chitin contained in the mycelium of fungi and yeasts. Prior art has repeatedly shown that in the cell walls of most yeast and fungi, chitin is associated with other polymers through covalent bonds, for example with polysaccharides of the β-glucans type, thereby forming a typical fibril structure. That is the reason why chitin is difficult to extract from the fungal and yeast biomass and to collect in a pure form. In order to obtain chitin chains, the chitin chains need to be separated from the other polymeric chains, preferably by a non-degrading method. The present invention discloses a method that allows separating chitin from other polymers, which comprise mainly β-glucans, without degradation of the chitin chains.

Chitin can be obtained from non-animal biomass, in particular from the cell walls of fungal mycelium or yeasts from several groups, including *Zygomycetes, Basidiomycetes, Ascomycetes* and *Deuteromycetes* and/or mixtures thereof, and preferably *Ascomycetes. Aspergillus* and yeasts like *Saccharomyces* belong to the latter group. In a preferred embodiment, the invention relates to a method characterized in that said biomass is selected from the group comprising but not limited to filamentous fungi or yeasts such as *Aspergillium, Penicillium, Trichoderma, Saccharomyces,* and *Schizosaccharomyces* species, and edible mushrooms such as *Agaricus, Pleurotus, Boletus,* and *Lentinula* species, and/or mixtures thereof. A common feature of these fungi and yeasts is the presence of chitin in their cell walls. In an even more preferred embodiment, said biomass is obtained from *Aspergillus niger*.

In another embodiment, the method is characterized in that said biomass is a side-product obtainable in a cultivation process wherein a fungal or yeast culture is used. Fungal mycelium can be collected in fungal cultures engineered for the industrial production of compounds like for example citric acid, enzymes, and antibiotics. Chitin can be extracted from cell walls of these cultivation side-products. In a preferred embodiment, said method is characterized in that said biomass is a side-product of a cultivation process wherein an *Aspergillus niger* culture is used for obtaining citric acid.

The method according to the invention comprises contacting said biomass with a basic solution, whereby an alkali-soluble fraction and alkali-insoluble are obtained and whereby said alkali-soluble fraction is discarded and said alkali-insoluble fraction comprising said cell wall derivatives is retained. The alkaline solution used to digest the fungal or yeast biomass is an aqueous solution of an alkali like sodium hydroxyde, potassium hydroxyde, ammonium hydroxyde, and preferably sodium or potassium hydroxyde. In a preferred embodiment, said basic solution comprises a concentration lower than 10% (w/v). The alkali concentration is preferably ranging between 0.1 and 15% (w/v), and is more preferably lower than 10%. The reaction is performed at a temperature preferably ranging between 5 and 120° C., and more preferably at a temperature lower than 60° C. The biomass is reacted in suspension in the alkaline solution at a concentration preferably ranging between 1 and 15% (dry weight, w/v), and more preferably between 3 and 12%. The reaction is preferably performed for 4 to 48 hours, and more preferably for less than 30 hours. This first extraction step allows to eliminate alkali-soluble compounds, including pigments, proteins, some lipids, and some polysaccharides.

In another preferred embodiment, the biomass can be treated in a first alkaline solution, filtrated and treated again in a second alkaline solution. Additives can be used in the alkaline suspension to improve the extraction of the alkali-insoluble product. Such additives may comprise but are not limited to organic solvents such as cyclohexane, ethyl acetate, methanol or ethanol; anti-foaming agents such as structol; tensio-active agents such as sodium dodecyl sulfate, poly (vinyl alcohol), tween or poloxamers; or enzymes preparations containing carboxylesterase, carboxylic ester hydrolase or triacylglycerol lipase (all synonym to EC 3.1.1.3).

For the isolation of the alkali-insoluble product of the biomass cell walls, which is a chitin-glucan copolymer in many fungal and yeast biomass, the first step is followed by repeated washing steps in water, followed by filtration and drying. For the isolation of chitin polymers, this first step is followed by repeated washing in water, followed by the further steps in the method as described below.

A second step in the method according to the invention comprises contacting said alkali-insoluble fraction with an acidic solution, by suspending said alkali-insoluble fraction and bringing said suspended fraction into contact with said acidic solution in order to obtain a suspension of an acidified alkali-insoluble fraction comprising said cell wall derivatives.

After a last filtration step as explained above, the alkali-insoluble product is suspended in water in order to obtain a concentration preferably between 1 and 8% (w/v), and more preferably between 1 and 5%. Then the pH of the aqueous suspension of the alkali-insoluble product is adjusted below 7.0 by addition of an acidic solution. The acidic solution is preferably an aqueous solution of an acid, for instance chlorhydric, acetic, formic, lactic, glutamic, aspartic, or glycolic acid, and preferably acetic acid. This step is preferably performed at a temperature between 5 and 60° C., more preferably below 30° C.

A third step in the method according to the invention comprises contacting said acidified alkali-insoluble fraction with β-glucanase enzymes whereby said cell wall derivatives are obtained. In a more preferred embodiment, the method is characterised in that the β-glucanase enzymes are selected from the group comprising endo-β(1,3)-glucanase, exo-β(1,3)-glucanase, β(1,3)(1,4)-glucanase, β(1,6)glucanase enzymes, or any mixture thereof. Even more preferred, a mixture of enzymes is added to the suspension of the acidified alkali-insoluble fraction, in order to hydrolyse the β-glucan chains that are associated with chitin. β-glucanase enzymatic activities can be easily found in commercial preparation of β-glucanases supplied by several companies. The hydrolysis reaction is preferably performed at a temperature between 5 and 60° C., and more preferably below 40° C. The reaction duration is preferably below 5 days.

Preferred preparations contain mainly β-glucanase activities, and preferably low or no chitinase activity. Commercially available enzyme preparations can be used, extracted from organisms like for example *Bacillus subtillis, Arthrobacter luteus, Penicillium emersoni, Penicillium funicolosum, Humicola insolens, Aspergillus niger, Trichoderma harzanium, Trichoderma longibrachiatum*. Said preparations are available from companies like NovoZymes, Erbsloh, Roche or Lyven. In order to hydrolyse the β-glucans chains of polysaccharides extracted from the cell walls of the fungal mycelium, preferred enzymatic preparation are those which contain the following β-glucanase activities: endo-β(1.3-1.4)-glucanase (EC 3.2.1.6); endo-β(1.3)-glucanase (EC 3.2.1.39); exo-β(1.3)-glucanase (EC 3.2.1.58); endo-β(1.6)-glucanase (EC 3.2.1.75); and/or β-glucosidase (EC 3.2.1.21, β-D-glucoside glucohydrolase). In example 3, provided below, several commercial enzymatic preparations are illustrated for use in the method according to the invention.

In a preferred embodiment the invention relates to a method characterized in that said cell wall derivatives are chitin-rich polymers (i.e. chitin polymers or chitin-rich chitin-glucan copolymers). The insoluble fraction obtained in the method mainly contains macromolecular chains of chitin, linked with a certain amount of residual oligomeric or macromolecular chains of β-glucan. The ratio of chitin to glucan can easily be adjusted by controlling the conditions of the reaction, mainly by the β-glucanase preparation employed and by the reaction duration. In a more preferred embodiment, the invention relates to a method characterized in that the relative amount of chitin is adjustable and preferably higher than 80%, and more preferably higher than 90% and even more preferably higher than 95%. The relative amount of chitin can be measured by solid-state $^{13}$C-NMR. Said chitin-rich insoluble fraction can also contain residual proteins, lipids and carbohydrates.

Optionally, in a further step of the present method, a second alkali solution is added at the end of the hydrolysis reaction, for example a solution of sodium hydroxide, potassium hydroxide, ammonium hydroxide, and preferably sodium or potassium hydroxide. This further step is preferably carried out at a temperature between 20 and 80° C., and more preferably below 70° C., preferably for a duration of 30 minutes to 3 hours, and more preferably below 2 hours. This second alkaline treatment allows the separation of chitin and β-glucan to be completed, thereby isolating chitin.

For the production of chitin polymers, the process is preferably continued with repeated washing steps, followed by a drying step.

In another aspect, the present invention relates to chitin polymers obtainable by the method according to the present invention. There are several advantages to the method disclosed in the invention. The method allows extracting pure chitin, partially or totally separated from the β-glucan chains. In contrast, other methods directly yield chitosan, chitin-glucan or chitosan-glucan products.

In a preferred embodiment, the chitin polymers contain more than 80% of chitin, and preferably more than 90% of chitin and even more preferred more than 95% chitin.

Furthermore, chitin obtained according to the present invention from fungal or yeast biomass, comprises lower crystalline index values than chitin polymers that are obtained from crustacean shells. In a preferred embodiment, the crystalline index of the chitin polymers is lower than 80%, and more preferably, below 70% and even more preferred below 65%, where chitin is obtained from an *Aspergillus niger* biomass. The crystalline index can be calculated by the method of Struszczyk et al. (*J. Appl. Polym. Sci.*, 1987, 33:177-189).

In another embodiment, the invention relates to chitin-rich chitin-glucan copolymers obtainable by the method according to the present invention. In a preferred embodiment, said chitin-rich chitin-glucan copolymers have an adjustable amount of chitin, which is preferably higher than 80%.

In yet another embodiment, the invention relates to chitin-glucan copolymers obtainable according to the present method, in particular, before the enzymatic hydrolysis step. In a preferred embodiment where chitin is obtained from an *Aspergillus niger* biomass, said chitin-glucan copolymers obtained before the enzymatic hydrolysis step contain an amount of chitin preferably comprised between 30 and 50%.

Moreover, the present method does not induce degradation of the chitin chains, in contrast to other methods, which make use of concentrated alkali solutions. The present extraction method does not require the use of aggressive surfactants, nor acidic compounds. The method yields chitin from a renewable source, for example a fungi or yeast biomass, which is a valuable alternative source for crustacean shells. Moreover, the alkali solutions used in the method can be recycled in the course of the extraction process.

Method for Preparing Chitosan

In another aspect, the present invention relates to methods for preparing chitosan. The present invention discloses the method for preparing chitosan having a higher molecular weight by a first process, and chitosan having a lower molecular weight by a second process.

In one process the invention relates to a method for preparing chitosan from chitin comprising the subsequent steps of
a) contacting said chitin with a basic solution, whereby an alkali-soluble fraction and an alkali-insoluble fraction is obtained and whereby said alkali-soluble fraction is discarded and said alkali-insoluble fraction comprising partially deacetylated chitin is retained,
b) contacting said alkali-insoluble fraction with an acidic solution, by suspending said alkali-insoluble fraction and bringing said suspended fraction into contact with said acidic solution in order to obtain a suspension of acidified alkali-insoluble fraction comprising said partially deacetylated chitin, and
c) contacting said acidified a suspension of alkali-insoluble fraction with a chitin deacetylase enzyme, whereby chitosan is obtained.

The chitin source for preparing chitosan in this method may comprise chitin of crustacean origin or chitin of fungal or yeast origin. In a preferred embodiment, the chitin source used is fungal chitin or yeast chitin obtainable by the above-described method according to this invention.

According to this method for preparing chitosan, chitin is treated in a concentrated solution of alkali so that the chitin chains are able to swell and that further access of chitin deacetylase to the chitin substrate is promoted. Preferred alkali solutions are sodium or potassium hydroxide solutions, used in amounts such that the weight ratio of alkali to chitin is ranging between 5 and 25, preferably between 10 and 25. To avoid chitin chains from degrading, and to promote the formation of a swollen chitin hydrogel, the alkali concentration is preferably as high as possible. In a preferred embodiment, said alkali solution comprises a concentration higher of 40% (w/v). The reaction takes place at a temperature of 50 to 120° C. In a preferred embodiment step a) is performed at a temperature comprised between 50 and 120° C., and more preferred between 80° C. and 120° C. In another preferred embodiment step a) is performed during a period comprised between 30 and 180 minutes, and preferably between 30 and 120 minutes. The alkali-insoluble fraction obtained in step a) is suspended and then diluted, filtrated and washed extensively with water.

Preferably, the alkaline solution used is collected after the first step, concentrated and recycled and re-used in the chitin isolation method of the present invention described above.

Then, the suspended alkali-insoluble fraction obtained is contacted with an acid solution, whereby an acidified fraction comprising partially deacetylated chitin is obtained. The pH of the suspension is adjusted to a value preferably below 7.0, and more preferably below 4.8, by addition of an acid, for example chlorhydric, acetic, formic, glutamic, phtalic acid, and preferably formic acid. This step takes place at room temperature.

Subsequently said acidified fraction obtained is contacted with a chitin deacetylase. Preferably a recombinant chitin deacetylase is used which is produced by a *Pichia pastoris* yeast that has been transformed with an expression vector carrying a DNA sequence encoding chitin deacetylase from *Mucor rouxii*. The recombinant chitin deacetylase (rCDA) to chitin ratio is preferably ranging between 0.5 and 10 mg/g chitin and more preferably between 0.5 and 5 mg/g. The deacetylase hydrolysis reaction is preferably performed at a temperature of 15 to 50° C., more preferably between 20 and 40° C., for duration of less than 120 hours, until the desired proportion of residual acetylated glucosamine units is reached.

It is important to note that this enzymatic step is performed under acid conditions. Preferably, the pH value during the enzymatic step is lower than 5.0, and even more preferred between 3.5 and 4.5. Unexpectedly, at this low pH values, good enzymatic deacetylation is obtained, although the optimal pH value of the recombinant deacetylase enzyme is comprised between 5.0 and 5.5. At the low pH values the enzyme remains active and the enzymatic deacetylation reaction can be advantageously performed within shorter times. Thus the CDA enzyme is used under reaction conditions which do not correspond to the optimal conditions for the stability and activity of the recombinant CDA enzyme. In fact, while the CDA enzyme is active under the optimal conditions of 60° C., and a pH preferably below 5.0, and more preferably comprised between 4.0 and 5.0, the present step is performed at different conditions, without being detrimental for the activity of the enzyme.

In a further embodiment, the method according to the invention comprises a further step which comprises precipitating said obtained chitosan. Herefore, the suspension is filtrated to eliminate non-deacetylated chitin chains, and the pH is adjusted to a value above 7.0 by addition of an alkali like sodium, potassium or ammonium hydroxide. The precipitated compound is then filtrated, washed, and either dried to yield chitosan in the amino form or resolubilized in acidic solution and freeze-dried. For example the precipitating compound can be solubilized in chlorhydric, acetic, citric, formic, lactic, glutamic, aspartic, glycolic, benzoic, sorbic (2,4-hexadienoic), oxalic, malic, tartric, ascorbic, lauric, or palmitic acid, or any other mineral or organic acid, or any other polyacid like for example hyaluronic acid or poly(acrylic acid).

This enzymatic method allows to recover higher molecular weight chitosan from chitin of fungal or crustacean origin, and also to control the final degree of acetylation at the desired value, by carefully choosing the conditions of the chitin deacetylase reaction, for example the pH or the duration of the reaction.

In another preferred embodiment of the present invention, the recombinant chitin deacetylase from *Mucor rouxii* expressed in *Pichia pastoris* (rCDA) can also be used to extend the deacetylation of chitosan, either from fungal or crustacean origin, with no loss of molecular weight.

For instance, a chitosan whose viscosimetric molecular weight is 500,000 Da and degree of acetylation is 19 mol % can be reacted with rCDA in a formic acid solution (1 N) at a polymer concentration of 0.5 g/l at pH 3.8 for 6 hours, at room temperature. The pH of the solution is then preferably increased over 7.0 by addition of an alkali like sodium, potassium or ammonium hydroxide to promote the precipitation of chitosan, which is preferably removed by filtration, subsequently washed and dried. In this example, the final degree of acetylation to comprised 10 mol %, and the molecular weight was not changed.

The enzymatic deacetylation method according to the invention for preparing chitosan advantageously allows producing highly deacetylated chitosan, with no loss of molecular weight and no loss of material, and no need for fractionation of the polymer chains. Since the method for producing the recombinant chitin deacetylase is a method intended for high volume fermentation batches, the amounts of chitin and chitosan that can be enzymatically transformed are suited for industrial production and use of the resulting highly deacetylated chitosan, in a very cost-effective and environmentally safe manner.

In a second process the invention relates to a method for preparing chitosan from fungal or yeast chitin comprising the subsequent steps of:

a) contacting said chitin with a basic solution, whereby an alkali-soluble fraction and an alkali-insoluble fraction is obtained and whereby said alkali-soluble fraction is discarded and said alkali-insoluble fraction is retained, b) contacting said alkali-insoluble fraction with an acidic solution, by suspending said alkali-insoluble fraction and bringing said suspended fraction into contact with said acidic solution whereby an acid-insoluble fraction and an acid-soluble fraction is obtained and whereby said acid-insoluble fraction is discarded and said acid-soluble fraction comprising chitosan is retained.

In a preferred embodiment, the chitin source used is fungal chitin or yeast chitin obtainable by the above-described method according to this invention.

The method for preparing low molecular weight chitosan consists in a strong alkaline reaction at high temperature. An alkali like sodium, potassium, lithium, or ammonium hydroxide, and preferably sodium or potassium hydroxide, is added to the chitin suspension, such as the weight ratio of alkali to the dry chitin mass is preferably ranging between 1 and 20 (w/w), and more preferably between 1 and 15 (w/w). Additive can be used to minimize the degradation of chitin chains, for example sodium borohydride, thiophenol, and organic solvents such as methanol, ethanol, can also be added.

Preferably, the alkaline solution used is collected after the first step, concentrated and recycled and re-used in the chitin isolation method of the present invention described above.

Subsequently, the obtained alkali-insoluble fraction is separated and suspended. In a preferred embodiment said step is performed at a temperature higher then 80° C. Preferably, the suspension is placed at a temperature ranging between 80 and 140° C., more preferably between 100 and 120° C., and the reaction preferably takes place for a duration ranging between 30 and 300 minutes, more preferably less than 240 min.

The alkali-insoluble fraction is removed by filtration and washed with water. It is then solubilized in a diluted acidic solution, for instance chlorhydric, acetic, formic, and preferably acetic acid at a concentration of 0.1 to 1N. The acid-insoluble fraction is eliminated by filtration.

In a further embodiment, the method comprises a further step wherein chitosan from said acid-soluble fraction is precipitated by contacting said fraction with a basic solution. The pH of the acid-soluble fraction is preferably raised above pH 8.0 with an alkali solution like of concentrated solution of sodium or ammonium hydroxide. The precipitating compound is filtrated, washed repeatedly with water, and dried. The obtained compound is chitosan under the amino form. In an example, a chitosan with a degree of acetylation of 14 mol % and a viscosimetric molecular weight of 20 kDa (as determined by capillary viscosimetry) can be obtained.

In a further embodiment, also chitosan salts can be obtained from the acid-soluble fraction. Therefore, the acid-soluble fraction is precipitated by addition of an alkali solution like sodium or ammonium hydroxide. The precipitating compound is filtrated, washed repeatedly with water, and then solubilized in an acidic solution and then freeze-dried from this acidic solution. The precipitating compound can be solubilized in chlorhydric, acetic, citric formic, lactic, glutamic, aspartic, glycolic, benzoic, sorbic (2,4-hexadienoic), oxalic, malic, tartric, ascorbic, lauric, or palmitic acid, or any other mineral or organic acid, or any other polyacid like for example hyaluronic acid or poly(acrylic acid).

In another embodiment, the invention relates to chitosan polymers obtainable by the method according to the present invention.

In a preferred embodiment, the present invention relates to chitosan polymers having an adjustable molecular weight. Depending on the process and the conditions of the deacetylation reaction, chitosan having a low, medium or high molecular weight is obtainable. Preferably, said chitosan has a molecular weight comprised between 10 and 1000 kDA, as determined by Ubbelohde capillary viscosimetry.

In another preferred embodiment, the present invention relates to chitosan polymers having an adjustable degree of deacetylation. Depending on the process and the conditions of the deacetylation reaction, the acetylation degree can be tuned, in a range preferably comprised between 0 and 40 mol %.

INDUSTRIAL APPLICATIONS

The present invention provides chitin polymers and chitin-rich chitin-glucan copolymers from non-animal origin obtainable by a method according to the present invention.

Chitin-glucan copolymers of the present invention, i.e. obtained before the enzymatic hydrolysis step according to the present method, comprise a portion of beta-glucan chains, the structure and composition of the copolymers being defined by the organism from which it is extracted. In a preferred embodiment, chitin-glucan copolymers are extracted from the mycelium of *Aspergillus niger*, and comprise mainly chitin and beta-(1,3)(1,4) and beta-(1,3) glucan chains. According to the invention, the amount of chitin and glucan in such polymers is further adjustable, depending on particular conditions applied during enzymatic hydrolysis, in order to obtain chitin-rich chitin-glucan copolymers.

Chitin polymers, (chitin-rich) chitin-glucan copolymers obtainable by a method according to the present invention provide interesting properties, which makes them suitable for being used in all kinds of applications. Major advantageous characteristics of these products include their wound healing properties and their chelating activity.

Also non-animal chitosan is obtainable by a method according to the present invention. Advantageously, starting from very pure chitin, very pure chitosan can be obtained. In addition, a controllable enzymatic deacetylation process enables to obtain chitosan of high molecular weight and at the same time an adjustable (low) degree of deacetylation. Also, due to the relative unlimited availability of fungal or yeast biomass large volumes of chitosan can be prepared, in a reproducible and adjustable way. Advantageously, such production is not subject to seasonal variation as it is the case when using a crustacean chitosan source.

Several problems are encountered when using chitosan from animal source in different applications. For instance, in nutritional application such chitosan is not suitable for vegetarians, can cause allergies to crustacean products, and requires the food products to be labelled accordingly. In cosmetic application such chitosan may cause allergy and there is a tendency for using non-animal products. Therefore, the non-animal chitosan obtainable by a method according to the present invention provides a solution for these issues.

Some of the interesting properties of the chitosan obtainable by a method according to the present invention include cationic charge, biodegradability, non-toxicity, chelating, wound healing, moisturizing. In addition the chitosan of the present invention does not induce allergic reactions and can provide an antifungal and antimicrobial activity.

Chitin and chitosan products obtainable according to the present invention may be used in multiple forms, depending on their application in various systems. Chitosan polymers may for instance be used in the form of an ammonium salt, as a diluted solution in different mineral and organic acids such as but not limited to chlorhydric, acetic, citric formic, lactic, glutamic, aspartic, glycolic, benzoic, sorbic (2,4-hexadienoic), oxalic, malic, tartric, ascorbic, lauric, or palmitic acid, or any other mineral or organic acid, any other polyacid like for example hyaluronic acid or poly(acrylic acid). The concentration of chitosan in such solution is preferably selected in function of the required viscosity. Therefore, according to the invention also solutions having different degrees of viscosity comprising chitin or chitosan products according to the present invention may be obtained.

Chitosan products obtainable according to the present invention can also be used in the form of a hydrogel. Such hydrogel may be prepared by using methods known in the art, for instance but not limited by preparation of a concentrated solution, by forming a complex with anionic (macro)molecules such as alginate, heparine, xanthan or pectin, by chemical crosslinking, or by forming covalent bonds between the amino-groups of the chitosan and other (macro)molecules. The products may also be used in the form of a thermo-reversible hydrogel.

Chitin and chitosan products obtainable according to the present invention may further be used in the form of a film. For instance, chitosan, prepared according to a method of the invention having a high molecular weight may have improved film-forming properties and can therefore provide more stable films. Also multi-layered membranes or substrates comprising chitosan in association with other polymers can be prepared.

Moreover, chitin and chitosan products obtainable according to the present invention can further be used to manufacture as porous films or porous object, from which the pore sizes are controllable by applying methods known by a person skilled in the art.

In another embodiment, chitin and chitosan products obtainable according to the present invention can be provided in the form of micro-, milli- or nano-particles, which can be obtained by techniques known by a person skilled in the art (e.g. see Polymeric Biomaterials, S Dimitriu ED, Marcel Dekker, 2002, Chap. 1). Chitosan products obtainable according to the present invention and provided in the form of particles can have multiple application possibilities including encapsulation of substances, organisms or active molecules such as seeds, cells, pigments, flavours, odorous substances, drugs, vaccines, bioactive (antibacterial or antifungal) agents, enzymes. The encapsulation in chitosan particles makes it possible to immobilize, protect, transport, or to release the active substances in a controlled way.

Chitin-glucan copolymers of the present invention are essentially not soluble in any solvent, although they are hydrophilic, and are therefore suitable for being used in the form of powder, fibers or in a lyophilised form.

In another embodiment of the present invention, composite material is provided comprising chitin polymers, (chitin-rich) chitin-glucan copolymers or chitosan polymers obtainable by a method according to the present invention. Chitin polymers or chitosan polymers of fungal origin according to the present invention can be used in a mixture with one or more other substances. It can for example be mixed with other polymers, the mixture being usable in one of the forms as mentioned above, in order to confer new properties or synergetic properties.

Chitin polymers, (chitin-rich) chitin-glucan copolymers or chitosan polymers obtainable by a method according to the present invention can be mixed with molecules of low molecular mass. In combination with other substances, chitin polymers, (chitin-rich) chitin-glucan copolymers or chitosan polymers obtainable by a method according to the present invention are also suitable as complexing agents, if the substance presents a negative charge, or suitable as matrix for the controlled release of a drug or an active agent or suitable as matrix for a cosmetic ingredient such as a pigment, a flavour, or an odorous substance.

Chitosan polymers obtainable by a method according to the present invention can also be mixed with a vaccine, wherein they are suitable as adjuvant. Chitin polymers, (chitin-rich) chitin-glucan copolymers or chitosan polymers can further also be mixed with an inorganic substances, for instance with ceramics, preferably calcium phosphates, whereby a matrix can be created which is suitable for supporting tissue regeneration such as a cartilage or bones.

Another embodiment of the present invention relates to derivatives of chitin polymers, (chitin-rich) chitin-glucan copolymers or chitosan polymers obtainable by a method according to the present invention. Chitin polymers, (chitin-rich) chitin-glucan copolymers or chitosan polymers are polymers that can be modified chemically to obtain derivatives, according to techniques known by a person skilled in the art. The chemical modification can for instance be carried out on one or more functional groups of the D-glucose, N-acetyl-D-glucosamine or D-glucosamine units, for example on the oxygen atom in position 6, or on the nitrogen atom in alpha of the carbon located in position 1 in the N-acetyl-D-glucosamine and D-glucosamine.

Chitin polymers, (chitin-rich) chitin-glucan copolymers or chitosan polymers obtainable by the methods according to the invention may be applied in various products and systems, preferably as in medical, pharmaceutical, agricultural, nutraceutical, food, textile, cosmetic, industrial and/or environmental applications.

In a preferred embodiment chitosan polymers according to the present invention may be used as excipient in the preparation of a medicament. They may be used in veterinary as well as human medical applications. The invention also relates to a pharmaceutical composition comprising chitosan polymers according to the present invention. To enable the use of chitosan in pharmaceutical forms, controlled and reproducible molecular weight distribution, degree of acetylation, and low and reproducible levels of impurities of the compounds are required. According to the methods of the present invention, compounds with such characteristics can be obtained.

Chitin polymers, (chitin-rich) chitin-glucan copolymers or chitosan polymers are not antigenic and are perfectly biocompatible. Moreover, they are biodegradable by enzymatic hydrolysis, for example in the presence of lyzozymes. Due to their anti-thrombogenic and haemostatic character they can be used in all fields of medicine. Therefore, chitin polymers, (chitin-rich) chitin-glucan copolymers or chitosan polymers obtainable by the methods according to the invention may be applied in wound healing systems. Chitin polymers, (chitin-rich) chitin-glucan copolymers or chitosan polymers obtainable by the methods according to the invention may also be used to prevent the formation of fibrin bits in wounds, and to prevent the formation of scars, and to support cell regeneration. Chitin polymers, (chitin-rich) chitin-glucan copolymers or chitosan polymers may be used in systems for tissue engineering, cell transplantation and cell encapsulation. Since the products may form air-permeable films, they can support cellular regeneration while protecting tissues from microbial aggressions. They may also be used to form sutures, bandages, and preferably to form degradable sutures and bandages. Chitosan polymers obtainable by the methods according to the invention are further suitable for manufacturing artificial skin and in systems for reconstruction of tissues and organs and/or the transplantation of cells. For example, chitin polymers, (chitin-rich) chitin-glucan copolymers or chitosan polymers may be used in systems for osseous repair in orthopaedics or orthodontics, for repair of the skin, the comea, the retina, the cartilage or for the reconstruction of organs as pancreas, stomach, and nervous systems.

Chitosan polymers according to the present invention are also suitable for use in contact lens, dry eye prevention compositions, as a tear substitute in the form of a topical hydrogel, as a topical carrier for ocular drugs, as a particulate or hydrogel systems for local delivery inside the eye, in devices to repair retinal detachment and macular degeneration and in surgical aids for surgery.

Due to good bio-adhesion properties, chitosan polymers according to the present invention can be applied as anti-adhesive surgical aid, for instance to prevent adhesion between tissues during surgery. They can also be applied as adjuvant for vaccines thanks to a good mucoadhesion.

Chitosan polymers obtainable according to the present invention can be further applied as support for transport and slow-release of active compounds in plants, animals and human. With regard to the oral administration forms of pharmaceuticals, it is particularly suitable to use chitosan polymers when encapsulated products must arrive without transformation in the intestine, since the products are not digested by the stomach. Chitosan can be formulated as particles, which gives even more opportunities for oral and parenteral controlled release applications. Chitosan can increase the efficacy of oral carriers by chemical modification and binding of drugs or other bio-functional molecules. Because chitosan polymers possess good film and gel forming properties, it can serve to manufacture transdermal membranes. Its muco-adhesive properties are desired for a good contact with the outer skin layer. Chitosan can also be useful to prepare innovative drug delivery systems for local and systemic routes of administration, like the vaginal, buccal, and parenteral routes.

Chitin polymers, (chitin-rich) chitin-glucan copolymers or chitosan polymers obtainable according to the present invention can be used as an excipient in the formation of tablets, the granulation of powders, the making of gels and films, the preparation of emulsions, and also as a wetting and coating agent. Some more original properties of chitosan can also be exploited in oral drug delivery systems, like its ability to provide a drug controlled release as a matrix, its bioadhesiveness, its film-forming properties, its ability to form complexes with anionic drugs and anionic polymers. Therefore, they may be used to in drug systems to improve the solubility of poorly water soluble drugs, to form hydrogels to enhance absorption of drugs across mucosal tissues, to potentiate immunological response of vaccines.

In another embodiment, chitin polymers, (chitin-rich) chitin-glucan copolymers or chitosan polymers obtainable according to the present invention can be further applied in agricultural and agrochemical systems. They may be applied as preservative coating and biofungicide when applied on fresh fruits, vegetables and crops, or as fertilizers, thereby increasing the number of useful soil microorganisms and decreasing harmful ones. Plant seeds may be soaked in aqueous solutions of chitosan to prevent microbial infections and increase plant production. Chitin polymers, (chitin-rich) chitin-glucan copolymers or chitosan polymers according to the present invention can further be used in solution, powder or coating of seeds. In low amounts, about a few milligrams per cubic meter of water, chitin polymers, (chitin-rich) chitin-glucan copolymers or chitosan polymers can be used to trigger plant defence mechanisms against parasitic infections and aggressions. In addition to anti-fungal properties, chitin polymers, (chitin-rich) chitin-glucan copolymers or chitosan polymers can be applied to reinforce the plants' root and to thicken the plants' stem. Chitin polymers, (chitin-rich) chitin-glucan copolymers or chitosan polymers according to the present invention can also be used to stimulate the synthesis of protective agents by a plant. Furthermore, they can be used to accelerate the germination and the growth of plants. In the agro-alimentary sector, they can be used for the coating of seeds, manure or pesticides.

Due to their film-forming properties, chitosan polymers of the invention may be used as additives in pesticides for providing a better contact and a better penetration of the pesticide. Furthermore, association of the pesticide with a small quantity of chitin or chitosan of the present invention may be suitable to decrease the amount of pesticide used.

In another embodiment, chitin polymers, (chitin-rich) chitin-glucan copolymers or chitosan polymers obtainable according to the present invention are further particularly suitable for use in nutraceutical and food applications. Chitin polymers, (chitin-rich) chitin-glucan copolymers or may be used as food supplements. In particular, chitosan polymers may be applied as food ingredient in dietetics. As chitosan polymers are not digested by the human body, they are suitable for behaving like a fibre, which is a significant element in a diet. As chitosan polymers bear cationic charges, they are able to complex negatively charged lipids and they are suitable for trapping lipids in the digestive tract. In addition, chitosan polymers may be applied in nutraceutical products for obtaining hypo-cholesterolemic effects.

In addition, chitosan polymers according to the present invention can be used as natural food additives for obtaining anti-microbial and anti-fungal activity against a wide range of food-borne fungi, yeast and bacteria. In addition, they may be used as adjuvant for conventional food preservatives, as anti-browning agents, as component for gas permeable edible films suitable for fruit/vegetable storage, as thickening, stabilizing or emulsifying agent, as thixotropic agents or as natural flavour extender. In addition, chitosan polymers according to the present invention may be used in food processes, where they may for instance be applied as foaming agents, as thickener or stabilizer. Due to their coagulant and flocculating capacities, chitosan polymers may also be applied in the clarification process of beverages like wine, beer and fruit juices. Herein they may precipitate compounds responsible for the haze of these beverages.

In another aspect of the food industry, chitosan polymers can also be used to prepare edible films and coatings to extend shelf life of fresh or processed food. Fungal chitosan polymers can be applied directly on fruits and vegetables, which allows extending shelf life, a better control of fruits/vegetable decay and delaying of ripening. Chitosan polymers are suitable as anti-browning agent on fruits and vegetables. They can then be used as an advantageous alternative to sulfite, the most effective browning inhibitor currently available although suspected to provoke adverse health effects.

In another aspect, the anti-microbial and anti-fungal activities of chitosan polymers according to the invention can be exploited in the food industry, for the preservation of meat, crustacean (oysters), fruits, vegetables and finished products, either alone or in synergetic combination with conventional preservatives like for example sulphite or sodium benzoate. When associated with other preservatives, it may be used to minimize the preservative concentration necessary for an inhibition effect.

In another embodiment, chitin polymers, (chitin-rich) chitin-glucan copolymers or chitosan polymers obtainable according to the present invention are further usable in textile applications. Chitosan polymers can for instance be applied on textile fibers in the form of a film by impregnating said fibers or a tissue with a solution. By doing so, the properties of the fibers or textiles may be changed, e.g. by application of chitin or chitosan such fibers or textiles may adopt an anti-bacterial character. Medical textiles can also be impregnated by chitin polymers, (chitin-rich) chitin-glucan copolymers or chitosan polymers according to the present invention and be suitable in systems for the treatment of wounds.

In cosmetic applications, chitin polymers, (chitin-rich) chitin-glucan copolymers or chitosan polymers obtainable according to the present invention are usable is compositions suitable for care of skin, such as creams, and for the hair, such as sprays, shampoos and after-shampoos, in make-up compositions, or in tooth pastes. They are further applicable in anti-UV compositions, in the preparation of deodorants, in compositions for oral hygiene and in compositions for encapsulation of pigments. The non-animal origin of the chitin or chitosan obtained according to the method described in the invention makes it possible to eliminate risks of allergies.

In environmental applications, chitin polymers, (chitin-rich) chitin-glucan copolymers or chitosan polymers obtainable according to the present invention may be applied as chelating agents, e.g. as heavy metal complexing agents. Chitin polymers, (chitin-rich) chitin-glucan copolymers or chitosan polymers may be applied for trapping heavy metals and in water purification techniques, or they can be applied in drinking water system for separating organic compounds and heavy metals. They can also be applied for treating water by precipitating certain waste and by capturing pollutants like DDT and polychlorobenzenes. In addition, they may also be used in applications wherein they are suitable for fixing radicals.

Moreover, chitin polymers, (chitin-rich) chitin-glucan copolymers or chitosan polymers according to the present invention may be used in the manufacturing process of paper. In this process they may replace some amino substituents such as gum or polysynthetic polysaccharides and they are suitable for reducing the use of chemical additives and to provide improved outputs. Paper produced by using chitin polymers, (chitin-rich) chitin-glucan copolymers or chitosan polymers according to the present invention may have a smoother surface and show better resistance to moisture. Moreover, chitin polymers, (chitin-rich) chitin-glucan copolymers or chitosan polymers according to the present invention may also be applied for production of sanitary paper, packing paper and paperboard.

EXAMPLES

Example 1

Alkaline Digestion of *Aspergillus niger* Mycelium

This example illustrates the first step in the method for isolating cell wall derivatives from fungal biomass according to the present invention. The biomass was obtained as side-product of a cultivation process for preparing citric acid using *Aspergillus niger*.

In this example, 995 g of the biomass containing 71% of water was collected and incubated in a reaction containing 2 liters of water and 93 g of sodium hydroxide pellets at room temperature, to reach a final biomass concentration of 3.4% (w/v). In this example, final concentration of NaOH comprised 10.6% (w/v) and the ratio of NaOH to biomass (dry weight) was 32%. After 26 hours, the mixture was filtered to collect the insoluble fraction of the residual biomass, which was washed repeatedly until neutral pH was obtained. In this example, the dry mass of the insoluble fraction was 145 g. The analysis of this fraction by $^{13}$C-NMR in solid phase revealed that mainly a mixture of chitin and glucan polymers were obtained. In this example, the ratio of chitin to glucan, as calculated from the solid-state $^{13}$C-NMR spectrum was 52:48±15 (w/w).

The chitin content in the insoluble fraction was determined by analysis of N-acetyl glucosamine released after hydrolysis of the insoluble fraction with chitinase and chitobiase enzymes, according to the method of Jeuniaux ("*Chitine et chitinolyse: un chapitre de biologie moléculaire*" 1963, Masson, Paris, 181) and Reissig et al. (*J. Biol. Chem.*, 1955, 217:959). The chitin content was also determined from nuclear magnetic resonance analysis of carbon 13 in solid phase ($^{13}$C-NMR) of the alkali-insoluble fraction obtained after alkaline digestion of the biomass. FIG. 1 represents the $^{13}$C RMN spectrum of the alkali-insoluble fraction comprising mainly a purified chitin-glucan polymer. After deconvolution and integration of the signals of the carbon atoms of N-acetyl-(D)-glucosamine and (D)-glucose units, the weight chitin:glucan ratio was calculated to be 41:59 (w/w).

Example 2

Alkaline Digestion of the Mycelium of *Aspergillus niger*

This example also illustrates the first step in the method for isolating cell wall derivatives from fungal biomass according to the present invention. The biomass was obtained as side-product of a cultivation process for preparing citric acid using *Aspergillus niger*.

In this example, the mycelium of *Aspergillus niger* was treated according to different conditions. Assays No. 1 to 4 were performed in a 10 L-reactor, and assays No. 5 to 6 in a 30 L-prototype reactor. Assays 1 to 5 were performed in one step, while assays 4' and 6 were performed in two steps. In assay No 4', the biomass was treated with a first NaOH solution (3.4%), then filtered and treated again in a second NaOH solution (2.8%). In assay No 6, the biomass was separated in two fractions successively placed in the reactor together with a low amount of NaOH followed by a higher amount of NaOH. Results are shown in Table 1.

TABLE 1

| No | $m_{mycelium}$ (g, dry) | $C_{mycelium}$ % (w/v) | $C_{NaOH}$ % (w/v) | T (° C.) | Duration (hours) | $m_F$ (% w/w) | ratio Ch:Gl* (w/w) |
|---|---|---|---|---|---|---|---|
| 1 | 289 | 10.6 | 3.4 | 26 | 25 | 50 | 41:59 ± 3 |
| 2 | 505 | 9.2 | 1.5 | 25 | 26 | 57 | N/D |
| 3 | 580 | 10.7 | 1.5 | 40 | 26 | 57 | 44:56 ± 2 |
| 4 | 313 | 5.2 | 1.7 | 25 | 24 | 50 | 32:68 |
| 4' | 485 | 10.6 | 3.4/2.8 | 25 | 24/6 | 40 | 37:63 |
| 5 | 496 | 2.9 | 2.0 | 25 | 22 | 49 | N/D |
| 6 | 446/446 | 2.9/2.9 | 2.0/4.0 | 25 | 22/18 | 49 | N/D |

$m_F$: proportion of final alkali-insoluble product to initial mycelium (dry mass)
N/D: not determined
*weight ratio of chitin to glucan as determined by $^{13}$C-NMR An extraction procedure applied to the alkali-insoluble fraction collected in assay No 4, as described by Folch et al. (1957, *J Biol Chem* 224:497-509), showed an amount of lipophilic compounds of 6% of the initial dry weight.

Figure 2:
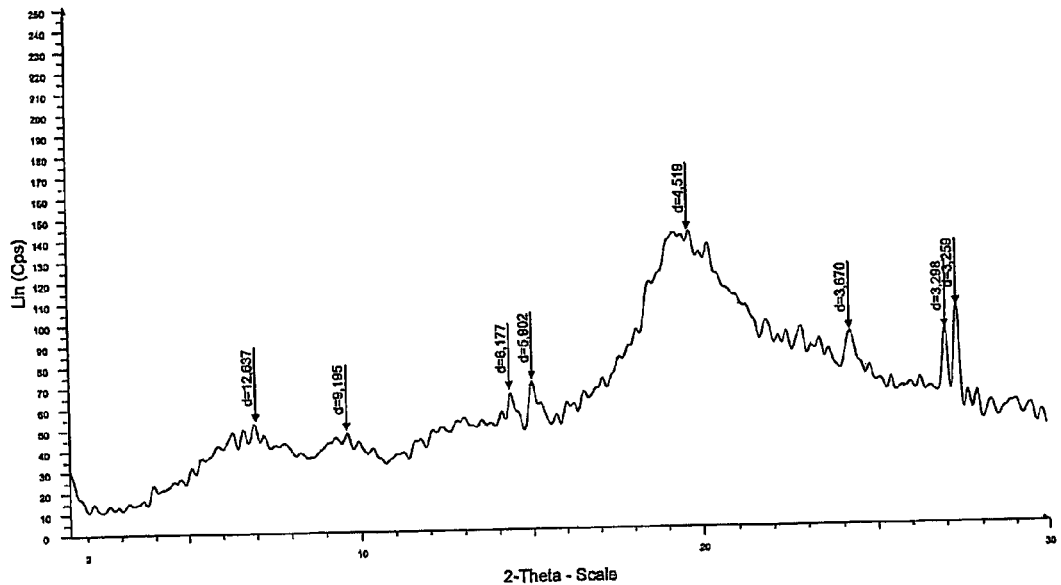
FIG. 2 represents a X-ray scattering study of the alkali-insoluble fraction obtained after alkaline digestion of fungal biomass according to the first step in the method for isolating cell wall derivates of the present invention, whose chitin:glucan ratio was 38:62±3 (w/w).

An X-ray scattering study (Siemens D5000, Cu—K$_\alpha$, λ=0.15406 nm, 2θ=1.5 à 30°, fente 1 mm, T=25° C.) of the alkali-insoluble fraction collected in assay No 4', whose chitin-glucan ratio was 37:63 (w/w), showed a large scattering band at 2θ=20° (FIG. 2), indicating a semi-crystalline structure. The crystalline index can be calculated as proposed by Yinhai et al. (*Chem. Mag.* 2002, 4:27) or Struszczyk et al. (*J. Appl. Polym. Sci.*, 1987, 33:177-189), as an indication of the proportion of crystalline over amorphous regions in the compound. According to the calculation of Struszczyk, the index of cristallinity (CrI) of this chitin-glucan alkali-insoluble compound was 64%, a value much lower than that found for a chitin sample extracted from shrimp shells and analyzed by X-ray scattering in the same conditions (CrI=87%).

Example 3

Enzymatic β-Glucanases Preparations

This example illustrates a preferred procedure for testing several commercial preparations of β-glucanases for use in a method according to the present invention. β-glucanase activity can be quantified from standard curves established with pure reference β-glucanase enzymes that are reacted with standard β-glucan substrates. For instance for testing EC 3.2.1.6 β-glucanase activity, lichenase (Megazyme) or β-glucanase (Fluka) can be reacted with barley β-glucan substrate (Megazyme), for testing EC 3.2.1.39 β-glucanase activity, an endo-β-(1,3) enzyme (Megazyme, Fluka) can be reacted with pachyman or curdlan substrates (Megazyme), for testing EC 3.2.1.58 activity, an exo-β-glucanase (Megazyme) can be reacted with laminarin or schleroglucan substrates (Sigma, Megazyme), and for testing EC 3.2.1.75 β-glucanase activity, a β-(1.6) glucanase can be reacted with pustulan (Sigma). The β-glucanase activity (in U, unit) is defined as the amount of enzyme needed to release 1 μmole of glucose per minute, at 37° C. after incubation with the standard substrate, at the recommended pH.

The protein amount contained in the commercial enzyme preparation can be determined by the BCA (bicinchoninic acid) method, which relies on the reduction of Cu(II) ions into Cu(I) ions by proteins, in alkali conditions. Cu(I) ions are able to form a complex with BCA, whose absorption at 526 nm is proportional with the protein concentration (PK Smith et al. (1985) *Anal. Biochem.* 150, 76). The specific β-glucanase activity (in U/mg) exhibited by the commercial preparations is the ratio of the enzymatic activity and the mass of protein contained in the preparation.

Enzymatic preparations which contain one or several of the β-glucanase activities listed above are preferably tested (see Table 2). In the testing procedure, combinations of selected enzymes are preferably investigated for their ability to hydrolyse the β-glucan chains of the alkali-insoluble fraction of digested mycelium of *Aspergillus niger*.

TABLE 2

β-glucanase activities found in commercial enzyme preparations (in U per mg of protein found in the preparation)

| Preparation No | 3.2.1.6 activity (U/mg protein) | 3.2.1.39 activity (U/mg protein) | 3.2.1.58 activity (U/mg protein) |
|---|---|---|---|
| 1 | 33 | 0 | 0 |
| 2 | 37 | 0 | 0 |
| 3 | 19 | 0 | 0 |
| 4 | 0 | 20 | 0 |
| 5 | 0 | 22 | 28 |
| 6 | 54 | 0 | 0 |
| 7 | 0 | 17 | 8 |
| 8 | 22 | 0 | 0 |

The β-glucanase hydrolysis reaction is preferably performed in the suspension of the alkali-insoluble fraction, which is obtained after alkaline treatment of biomass according to the present invention, at a pH preferably comprised between 4.0 and 7.0, and more preferably between 4.5 and 6.8. A mixture of β-glucanase preparations, for example a mixture of endo-β(1,3), exo-β-(1,3) and endo-β-(1,3)(1,4)-glucanase enzymes, is added to the suspension. To hydrolyse the β-glucan chains of the chitin-glucan extracted from an *Aspergillus niger* biomass, the proportion of β-glucanases, as expressed in unit of activity per mass of dry digested biomass, preferably ranges between 5 and 1500 U/g, and more preferably between 20 and 500 U/g. The digested biomass concentration preferably ranges between 0.5 and 15% (w/v), and more preferably between 2 and 8% (w/v). The preferred reaction temperature is below 40° C. The duration of the hydrolysis reaction ranges between 1 and 8 days, preferably below 5 days.

Example 4

Isolation of Cell Wall Derivates from *Aspergillus niger* Biomass According to the Invention This example illustrates the isolation of cell wall derivatives from fungal biomass according to a method of the present invention. The biomass was obtained as side-product of a cultivation process for preparing citric acid using *Aspergillus niger*.

In this example, 3.3 kg of the biomass, containing 71% of water, 7.2 liters water and 320 g of NaOH pellets were placed in a reactor at room temperature. After 26 hours, the mixture was filtered to collect the insoluble fraction of the residual biomass, which was washed three times. The alkali-insoluble fraction was collected and suspended in 4 liters of water. The pH of the suspension was adjusted at 5.5 by addition of glacial acetic acid. To the acidified suspension, 13.2 g of the β-glucanase preparation No 5 (see Table 2), and 8.25 ml of the beta-glucanase preparation No 6 (see Table 2) were added. The reaction was carried out at 37° C. for 4 days. The suspension was then filtered, and the insoluble fraction washed in water and freeze-dried, to yield a mass of 34% of the initial chitin-glucan. For this example, the solid-state $^{13}$C-NMR spectrum of the compound revealed the presence of chitin and residual β-glucan polymers, with a chitin:glucan ratio of 94:6±14 (w/w).

Example 5

Beta-glucanase Hydrolysis of a Chitin-Glucan Fraction of *Aspergillus niger* Biomass This example illustrates the β-glucanase hydrolysis reaction performed in a method for isolating cell wall derivatives from fungal biomass according to the present invention.

In this example, the β-glucanase hydrolysis reaction was performed in different conditions, with variable amounts of commercial beta-glucanase preparations Nos 2, 5, and 6 (see Table 2), and for a duration of 5 days. The starting compound to be hydrolyzed was a freeze-dried chitin-glucan conjugate extracted from the mycelium of *Aspergillus niger* according to a method as described above, whose ratio of chitin to glucan was either 32:68 (assay No 1) or 38:62 (assays Nos 2 to 7). Results are shown in Table 3.

Figure 3:
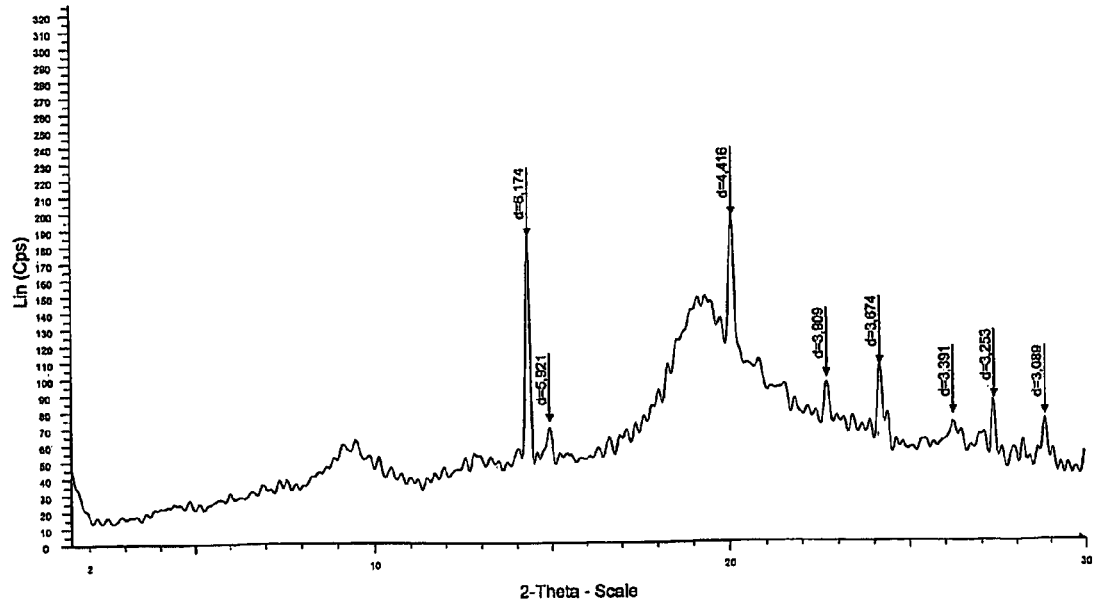
FIG. 3 represents a X-ray scattering study of the alkali-insoluble fraction obtained after alkaline digestion of fungal biomass according to the first step in the method for isolating cell wall derivates of the present invention, whose chitin:glucan ratio was 85:15±8 (w/w).

The X-ray scattering study (Siemens D5000, Cu—$K_\alpha$, $\lambda$=0.15406 nm, 2θ=1.5 to 30°, fente 1 mm, T=25° C.) of the chitin-rich alkali-insoluble fraction of assay No 2, whose chitin-glucan ratio was 85:15±8 (w/w), showed a large scattering band at 2θ=20° (FIG. 3). In this example, the crystalline index of the compound calculated according to Struszczyk et al. (*J. Appl. Polym. Sci.* (1987) 33, 177-189) was 67%, while it is 87% for chitin extracted from shrimp shells.

Example 6

Preparation of Fungal Chitosan from Chitin

This example illustrates the preparation of chitosan from chitin obtained after β-glucanase hydrolysis of a chitin:glucan fraction of *Aspergillus niger* mycelium.

4 g of the insoluble fraction obtained by beta-glucanase hydrolysis in example 4, 40 g of NaOH and 40 ml of water were placed at 120° C. for 1 hour. The obtained suspension was suspended in 200 ml of water, and acetic acid was added to reach a pH of 3.5. After 12 hours, the solution was filtrated, and the filtrate was collected. In this example, the pH of the filtrate was adjusted to 9.5 by addition of ammonium hydroxide to promote the precipitation of chitosan. After centrifugation, washing and freeze-drying, 1 g of the acid-soluble fraction was obtained. In this example, the solid-state $^{13}$C-NMR spectrum of the compound revealed that the acid-soluble fraction was pure chitosan, with no residual β-glucan chains. The proportion of N-acetyl-D-glucosamine was 14 mol % and the viscosimetric molecular weight was around 20,000 Da, as measured by Ubbelohde capillary viscosimetry.

Example 7

Preparation of Fungal Chitosan Chloride from Chitin

This example illustrates the preparation of chitosan chloride from chitin obtained after beta-glucanase hydrolysis of a chitin-glucan fraction of *Aspergillus niger* mycelium.

In this example, 60 g of a chitin-rich insoluble fraction obtained by β-glucanase hydrolysis as e.g. in example 4, 300 g of NaOH, 6 g of sodium boron hydride, and 300 g of water were placed at 120° C. for 1 hour. The obtained suspension was then centrifuged, filtered and washed until low conductivity. The insoluble fraction was suspended in 200 ml of acetic acid 0.5 M. After 12 hours, the solution was filtrated, and the filtrate was collected. In this example, the pH of the

TABLE 3

| N° | ratio Ch:Gl$_0$ (w/w) | m$_0$ (g dry) | C$_{Ch-Gl}$ % (w/v) | Enzyme 5 (mg/g) | Enzyme 6 (mg/g) | Enzyme 2 (mg/g) | m$_F$ (%) | ratio Ch:Gl$_F$ (w/w) |
|---|---|---|---|---|---|---|---|---|
| 1 | 32:68 | 2.0 | 4.4 | 12.5 | 27.5 | 0 | 37 | 100:0 ± 5 |
| 2 | 38:62 | 2.7 | 8.6 | 13 | 28 | 0 | 37 | 85:15 ± 8 |
| 3 | 38:62 | 1.9 | 4.2 | 56 | 33 | 0 | 38 | 96:4 ± 22 |
| 4 | 38:62 | 1.9 | 4.2 | 29 | 0 | 0 | 48 | 104:0 ± 23 |
| 5 | 38:62 | 1.9 | 4.2 | 12 | 33 | 0 | 39 | 105:0 ± 23 |
| 6 | 38:62 | 1.9 | 4.2 | 12 | 0 | 160 | 41 | 96:4 ± 21 |
| 7 | 38:62 | 1.9 | 4.2 | 6 | 16 | 0 | 46 | 80:20 ± 9 | m$_F$: proportion of final alkali-insoluble product to initial mycelium (dry mass);
ratio Ch:Gl$_F$: ratio of chitin to glucan as determined by $^{13}$C-NMR.

filtrate was adjusted to 9.5 by addition of ammonium hydroxide to promote the precipitation of chitosan. After centrifugation and washing, the acid-soluble fraction was solubilized in 28 ml of HCl 1N at pH 3.6. The solution was then freeze-dried, yielding 6 g of chitosan under the ammonium chloride form. The proportion of N-acetyl-glucosamine is 17 mol % and the viscosimetric molecular weight is around 20,000 Da.

Example 8

Preparation of High Molecular Weight Chitosan with Low Degree of Acetylation by Enzymatic Deacetylation of Chitin In this example, commercial chitin from shrimp shells was treated in different conditions in order to yield chitosan. First, it was treated with a strong alkaline solution of NaOH at variable concentration and NaOH:chitin ratio, in order to transform chitin into a gel form and to induce partial deacetylation of N-acetyl-glucosamine into glucosamine units. Then, the partially deacetylated chitin was filtrated, washed, and resuspended in solution of sodium phtalate (10 mM) at pH 5.5 to yield a chitin concentration of 5% (w/v). Subsequently, a recombinant chitin deacetylase enzyme (rCDA) was added, to reach a rCDA:chitin ratio of 5:1000, and the suspension was placed at 37° C. for 5 days. To estimate the extend of deacetylation promoted by rCDA, the released acetic acid was assessed. The suspension was filtered, and the alkali-insoluble fraction was washed with water and dried. It was then solubilized in a solution of acetic acid, filtrated, and then pH was raised by addition of ammonium hydroxide to promote the precipitation of chitosan chains. The precipitate was then washed and dried. Results of the assays are represented in Table 4.

observed in assays Nos 5 to 8 of this example, chitin preferably is in a gelled form when the alkali concentration is above 50% (w/w), and is preferably sufficiently pre-deacetylated, in order to allow the rCDA to catalyse the deacetylation reaction.

Example 9

Preparation of High Molecular Weight Chitosan by Enzymatic Deacetylation of Chitosan This example illustrates the preparation of chitosan having a high molecular weight and a low degree of acetylation by enzymatic deacetylation of chitosan. Various chitosan samples characterized by their initial viscosimetric molecular weight ($Mv_0$) and degree of acetylation ($DA_0$) were reacted with the recombinant chitin deacetylase (rCDA), in order to decrease the degree of acetylation to a lower value ($DA_F$). In this series of assays, the reaction medium was either a non buffered solution of chlorhydric 1 N (assays No 1 to 4) or formic acid 1N (assays Nos 5 to 10) or a buffered solution of formic acid 1N with sodium phtalate or (No 10) or glutamate (No 11) at varying pH. In this example, the ratio of rCDA to chitosan was either 1:1000 (No 4) or 5:1000.

TABLE 4

| No | t (min) | T (° C.) | $C_{NaOH}$ % (w/w) | $C_{chitin}$ % (w/v) | NaOH:chitin (w/w) | $m_F$ (%) | DA* (mol %) | Aspect | $D_{DA}$** (%) |
|---|---|---|---|---|---|---|---|---|---|
| 1 | 30 | 100 | 30 | 7 | 6 | 100 | 87 | X | <10 |
| 2 | 30 | 100 | 40 | 8 | 8 | 76 | 64 | X | <10 |
| 3 | 30 | 80 | 50 | 10 | 10 | 75 | 75 | X | <20 |
| 4 | 30 | 80 | 50 | 10 | 10 | 88 | 82 | X | <20 |
| 5 | 60 | 80 | 50 | 10 | 10 | 45 | 68 | Gel | >20 |
| 5' | 60 | 80 | 50 | 10 | 10 | 60 | 57 | Gel | >20 |
| 6 | 30 | 100 | 50 | 4 | 25 | 46 | 72 | Gel | <20 |
| 7 | 30 | 110 | 50 | 10 | 10 | 51 | 53 | Gel | >20 |
| 8 | 60 | 110 | 50 | 10 | 10 | 43 | 39 | Gel | >20 |

$m_F$: mass of chitin after the treatment in alkali;

*DA: degree of acetylation of chitin after alkaline treatment;

**$D_{DA}$: difference in degree of acetylation of the acid-soluble fraction of alkali-treated chitin before and after reaction with rCDA (efficiency of the CDAse reaction)

In this example, the efficiency of the rCDA enzyme, as shown by the difference in DA before and after reaction with rCDA ($D_{DA}$), depended on the previous alkali treatment, mainly the NaOH concentration and the temperature. As Chitosan was then recovered as described in the above-given examples, by precipitation at pH above 7.0. Results of the assays are represented in Table 5. For all samples, the final viscosimetric molecular weight was unchanged.

TABLE 5

| No. | $DA_0$ mol % | $Mv_0$ kDa | Cp (% w/v) | Solution | pH | T (hrs) | T (° C.) | $C_{CDA}$ (g/kg) | $DA_F$ (mol %) |
|---|---|---|---|---|---|---|---|---|---|
| 1 | 19 | 500 | 0.5 | HCl 1N | 3.8 | 6 | 20 | 5 | 11 |
| 2 | 19 | 500 | 0.5 | HCl 1N | 4.6 | 6 | 20 | 5 | 21 |
| 3 | 19 | 500 | 0.5 | HCl 1N | 3.6 | 3 | 20 | 5 | 12 |
| 4 | 19 | 500 | 1.0 | HCl 1N | 3.8 | 6 | 20 | 1 | 13 |
| 5 | 19 | 500 | 0.5 | Formic acid 1N | 3.8 | 6 | 20 | 5 | 12 |
| 6 | 19 | 500 | 0.5 | Formic acid 1N | 3.8 | 6 | 50 | 5 | 20 |
| 7 | 17 | 142 | 0.5 | Formic acid 1N | 3.8 | 6 | 20 | 5 | 11 |
| 8 | 12 | 225 | 0.5 | Formic acid 1N | 3.8 | 6 | 20 | 5 | 10 |
| 9 | 13 | 245 | 0.5 | Fomilc acid 1N | 3.8 | 6 | 20 | 5 | 10 |
| 10 | 19 | 500 | 0.5 | Phtalate 10M, formic acid 1N | 4.6 | 6 | 20 | 5 | 11 |
| 11 | 19 | 500 | 0.5 | Glutamate 10M, formic acid 1N | 4.8 | 6 | 20 | 5 | 14 |

Example 10

Preparation of a Porous Support Comprising Chitosan

Chitosan obtained according to a method of the present invention can be used for the preparation of films or porous objects, whose size of the pores is controlled.

For example, particles of gauged size consisting of water-soluble molecules (e.g. sodium chloride) can be mixed with chitosan in an acid solution. Then this chitosan matrix is solidified by solvent evaporation or freeze-drying. The particles are eliminated by washing to generate the pores.

Porous matrices comprising chitosan can also be prepared by means of polymer/solvent phase separation of the liquid to solid or liquid to liquid type, which were thermically induced. For example, chitosan is dissolved in a solvent such as a concentrated or diluted organic acid, for example acetic acid or formic acid, and is subsequently frozen at a temperature lower than the temperature of solidification of the solvent (freezing point), and then freeze-dried. The pores are generated at the place of the solvent crystals, crystals that are formed at the time of freezing by a mechanism of transition from liquid to solid phase. A transition from liquid to liquid phase can also be induced by dissolving chitosan in a solvent mixture of a solvent and a non solvent (both able to be freeze-dried). The solvent may be a concentrated organic acid such as acetic or formic acid. The size and the distribution of the pores depend on the mechanism of transition from polymer/solvent phase.

What is claimed is:

1. A method for preparing chitosan from fungal or yeast chitin comprising the subsequent steps of:
   a) isolating chitin polymers or chitin-rich chitin-glucan copolymers from fungal or yeast biomass,
   b) contacting said isolated chitin polymers or chitin-rich chitin-glucan copolymers with an alkaline solution at a temperature of 100 to 120° C. for 30 to 300 minutes at a weight ratio of alkali to the amount of dry chitin contained in the chitin polymers or chitin rich chitin-glucan co-polymers of step a) which is between 1 and 20 (w/w), whereby an alkali-soluble fraction and an alkali-insoluble fraction is obtained and whereby said alkali-soluble fraction is discarded and said alkali-insoluble fraction is retained,
   c) contacting said alkali-insoluble fraction with an acidic solution, by suspending said alkali-insoluble fraction and bringing said suspended fraction into contact with said acidic solution whereby an acid-insoluble fraction and an acid-soluble fraction is obtained and whereby said acid-insoluble fraction is discarded and said acid-soluble fraction comprising chitosan is retained.

2. The method for preparing chitosan according to claim 1, wherein a further step is provided which comprises precipitating chitosan from said acid-soluble fraction by contacting said fraction with a basic solution.

3. A method for preparing chitosan from fungal or yeast chitin comprising the subsequent steps of:
   a) isolating chitin polymers or chitin-rich chitin glucan copolymers from fungal or yeast biomass by the subsequent steps of:
      i. contacting said biomass with a basic solution having a concentration ranging between 0.1 and 15% w/v at a temperature lower than 60° C. for less than 30 hours, whereby an alkali-soluble fraction and an alkali-insoluble fraction are obtained and whereby said alkali-soluble fraction is discarded and said alkali-insoluble fraction is retained,
      ii. contacting said alkali-insoluble fraction with an acidic solution, by suspending said alkali-insoluble fraction in water and bringing the pH of said suspended fraction to below 7.0 by bringing said suspended fraction into contact with said acidic solution at a temperature of below 30° C. in order to obtain a suspension of acidified alkali-insoluble fraction whereby chitin polymers or chitin-rich chitin glucan copolymers are obtained,
   b) contacting said isolated chitin polymers or chitin-rich chitin glucan copolymers with an alkaline solution at a temperature of 100 to 120° C. during 30 to 300 minutes at a weight ratio of alkali to the amount of dry chitin contained in the chitin polymers or chitin rich chitin-glucan co-polymers of step a) which is between 1 and 20 (w/w), whereby an alkali-soluble fraction and an alkali-insoluble fraction is obtained and whereby said alkali-soluble fraction is discarded and said alkali-insoluble fraction is retained,
   c) contacting said alkali-insoluble fraction with an acidic solution, by suspending said alkali-insoluble fraction and bringing said suspended fraction into contact with said acidic solution whereby an acid-insoluble fraction and an acid-soluble fraction is obtained and whereby said acid-insoluble fraction is discarded and said acid-soluble fraction comprising chitosan is retained.

4. A method for preparing chitosan from fungal or yeast chitin comprising the subsequent steps of:
   a) isolating chitin polymers or chitin-rich chitin glucan copolymers from fungal or yeast biomass, by the subsequent steps of:

i. contacting said biomass with a basic solution having a concentration ranging between 0.1 and 15% w/v at a temperature lower than 60° C. for less than 30 hours, whereby an alkali-soluble fraction and an alkali-insoluble fraction are obtained and whereby said alkali-soluble fraction is discarded and said alkali-insoluble fraction is retained, ii. contacting said alkali-insoluble fraction with an acidic solution, by suspending said alkali-insoluble fraction in water and bringing the pH of said suspended fraction to below 7.0 by bringing said suspended fraction into contact with said acidic solution at a temperature of below 30° C. in order to obtain a suspension of acidified alkali-insoluble fraction whereby chitin polymers or chitin-rich chitin glucan copolymers are obtained, and iii. contacting said acidified suspension of alkali-insoluble fraction with β-glucanase enzymes whereby chitin polymers having an amount of chitin which is higher than 80%, or chitin-rich chitin glucan copolymers having an amount of chitin which is higher than 80% are obtained, b) contacting said isolated chitin polymers or chitin-rich chitin glucan copolymers with an alkaline solution at a temperature of 100 to 120° C. during 30 to 300 minutes at a weight ratio of alkali to the amount of dry chitin contained in the chitin polymers or chitin rich chitin-glucan co-polymers of step a) which is between 1 and 20 (w/w), whereby an alkali-soluble fraction and an alkali-insoluble fraction is obtained and whereby said alkali-soluble fraction is discarded and said alkali-insoluble fraction is retained, c) contacting said alkali-insoluble fraction with an acidic solution, by suspending said alkali-insoluble fraction and bringing said suspended fraction into contact with said acidic solution whereby an acid-insoluble fraction and an acid-soluble fraction is obtained and whereby said acid-insoluble fraction is discarded and said acid-soluble fraction comprising chitosan is retained.

* * * * *

UNITED STATES PATENT AND TRADEMARK OFFICE
CERTIFICATE OF CORRECTION

PATENT NO. : 7,556,946 B2  Page 1 of 1
APPLICATION NO. : 10/504046
DATED : July 7, 2009
INVENTOR(S) : Versali et al.

It is certified that error appears in the above-identified patent and that said Letters Patent is hereby corrected as shown below:

On the title page item (56),

Column 2, Line 6, Other Publications, "Chitosan Coatinig on" should be changed to --Chitosan Coating on--

Page 2, Column 1, Line 2, Other Publications, ""Space Effects on" should be changed to --"Spacer Effects on--

Column 1, Line 55, "crustacean cuticule," should be changed to --crustacean cuticle,--

Column 2, Line 52, "and deproteneisation by" should be changed to --and deproteinization to--

Column 5, Line 41, "capillary Ubbleohde" should be changed to --capillary Ubbelohde--

Column 8, Line 54, "*Penicillium emersoni*," should be changed to --*Penicillium emersonii*,--

Column 10, Line 57, "phtalic acid," should be changed to --phthalic acid,--

Column 15, Line 42, "presence of lyzozymes." should be changed to --presence of lysozymes.--

Column 15, Line 63, "the comea, the" should be changed to --the cornea, the--

Column 23, Line 21, "of sodium phtalate" should be changed to --of sodium phthalate--

Column 25, Line 12, Table 5, "Fomilc acid IN" should be changed to --Formic acid IN--

Column 25, Line 13, Table 5, "Phtalate 10M," should be changed to --Phthalate 10M,--

Signed and Sealed this

Twenty-sixth Day of January, 2010

David J. Kappos
*Director of the United States Patent and Trademark Office*